United States Patent [19]
Bergstrand et al.

[11] Patent Number: 6,103,697
[45] Date of Patent: Aug. 15, 2000

[54] PEPTIDES WITH IMMUNOMODULATORY EFFECTS

[75] Inventors: Håkan Bergstrand, Bjärred; Tomas Eriksson, Lund; Kostas Karabelas, Lund; Magnus Lindvall, Lund; Bengt Särnstrand, Lund, all of Sweden

[73] Assignee: Astra Aktiebolag, Sodertalje, Sweden

[21] Appl. No.: 08/836,480

[22] PCT Filed: Oct. 6, 1995

[86] PCT No.: PCT/SE95/01151

§ 371 Date: Apr. 14, 1997

§ 102(e) Date: Apr. 14, 1997

[87] PCT Pub. No.: WO96/11943

PCT Pub. Date: Apr. 25, 1996

[30] Foreign Application Priority Data

Oct. 14, 1994 [SE] Sweden .................................. 9403526

[51] Int. Cl.$^7$ ........................... A61K 38/08; A61K 38/10
[52] U.S. Cl. ................................. 514/14; 514/15; 514/16; 514/17; 514/18; 530/327; 530/328; 530/329; 530/330; 530/332; 424/278.1; 424/280.1
[58] Field of Search ..................................... 530/327–330; 514/14–18; 426/278.1, 280.1

[56] References Cited

U.S. PATENT DOCUMENTS

| | | |
|---|---|---|
| 4,585,755 | 4/1986 | Morgan et al. . |
| 4,822,606 | 4/1989 | Snyderman et al. . |
| 5,223,485 | 6/1993 | Kawai et al. . |

FOREIGN PATENT DOCUMENTS

WO 95/01182  1/1995  WIPO .

OTHER PUBLICATIONS

Nicolas, e et al. Tetrahedron, 51(19), 5701–10, Aug. 1995.
Cheronis et al. J. Med. Chem., 35(9), 1563–72, Sep. 1992.
Burton, J. et al. J. Med. Chem., 31(8), 1647–51, Aug. 1988.
Balcewicz–Sablinska et al., "Human Eosinophil Cytotoxicity–Enhancing Factor", The Journal of Immunology, 147:2170–2174 (1991).
Bergstrand et al., "Stimuli–Induced Superoxide Radical Generation in Vitro By Human Alveolar . . . ", Journal of Free Radicals in Biology & Medicine 2:119–127 (1986).
Bushweller et al., "Structural and Functional Characterization of the Mutant *Escherichia Coli* . . . ", Biochemistry 31:9288–9293 (1992).
Chen et al., "Costimulation of T cells for tumor immunity", Immunology Today 14:483–486 (1993).
Clarke et al., "Identification of molecules involved in the early pregnancy factor phenomenon", J. Reprod. Fert. 93:525–539 (1991).
Deiss et al., "A Genetic Tool Used to Identify Thioredoxin as a Mediator of a Growth Inhibitory Signal", Science 252:117–120 (1991).
Espinoza–Delgado et al., "Regulation of IL–2 Receptor Subunit Genes in Human Monocytes", Journal of Immunology 149:2961–2968 (1992).
Grasso et al., "A synthetic peptide corresponding to hFSH–B–(81–95) has thioredoxin–like activity", Molecular and Cellular Endocrinology 78:163–170 (1991).
Grippo et al., "Proof that the endogenous, Heat–stable Glucocorticoid Receptor Activating Factor is Thioredoxin", Journal of Biological Chemistry 260:93–97 (1985).
Hansson et al., "T lymphocytes inhibit the vascular response to injury", Proc. Natl. Acad. Sci, USA 88:10530–10534 (1991).
Arne Holmgren, "Thioredoxin and Glutaredoxin Systems", The Journal of Biological Chemistry 264:13963–13966 (1989).
Cornelis J.M. Melief, "Tumor Eradication by Adoptive Transfer of Cytotoxic T Lymphocytes", Advances in Cancer Research 58:143–174 (1992).
Noiva et al., "Protein Disulfide Isomerase", The Journal of Biological Chemistry 267:3553–3556 (1992).
Paupe, Jean,"Immunotherapy with an Oral Bacterial Extract (OM–85 BV) for Upper Respiratory Infections", Respiration:International Review of Thoracic Disease 58:150–154 (1991).
Radermecker et al., "Increase in the number and the phagocytic function of Guinea Pig pulmonary . . . ", Int. J. Immunopharmac. 10:913–917 (1988).
Rosenberg, Steven A., "Immunotherapy of cancer using interleukin 2", Immunology Today 9:58–62 (1988).
Roszman et al., "Modulation of T–cell function by gliomas", Immunology Today 12:370–374 (1991).
Ruiz–Gayo et al., "Uteroglobin–Like Peptide cavities I. Synthesis of antiparallel and parallel dimers . . . ", Tetrahedron Letters 29:3845–3848 (1988).
Shimotohno et al., "Identification of new gene products coded from X regions of human T–cell leukemia viruses", Proc. Natl. Acad. Sci, USA 82:302–306 (1985).
Stevenson, Freda K., "Tumor vaccines", FASEB J. 5:2250–2257 (1991).
Van Wauwe et al., "On the Biochemical Mode of Action of Levamisole: an update", Int. J. Immunopharmic. 13:3–9 (1991).
Varela et al., "Second generation immune networks", Immunology Today 12:159–166 (1991).
Yodoi et al., "Diseases associated with HTLV–I: virus, IL–2 receptor dysregulation and redox regulation", Immunology Today 13:405–411 (1992).
International Search Report: International Application No. PCT/SE 95/01151; (Oct. 6, 1995).

*Primary Examiner*—Michael P. Woodward
*Assistant Examiner*—Michael Borin
*Attorney, Agent, or Firm*—Fish & Richardson P.C.

[57] ABSTRACT

Novel homodimers that include cysteine-containing peptides having 4–15 amino acid residues can be administered to modulate the immune response in an animal.

14 Claims, No Drawings

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:1:

Gly Pro Cys Ile
1

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:2:

Gly Pro Cys Gly
1

(2) INFORMATION FOR SEQ ID NO:3:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:3:

Ala Pro Cys Ala
1

(2) INFORMATION FOR SEQ ID NO:4:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:4:

Ile Pro Cys Tyr
1

(2) INFORMATION FOR SEQ ID NO:5:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:5:

```
Phe Gly Pro Cys Ile
 1               5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 6...6
        (D) OTHER INFORMATION: where Xaa at position 6 is "Asn-NH2"

(xi) SEQUENCE DESCRIPTION: SEQ ID NO:6:

Gly Pro Cys Ile Leu Xaa
 1               5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:7:

Gly Pro Cys Ile Leu Asn Arg
 1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:8:

Leu Leu Phe Gly Pro Cys Ile
 1               5

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:9:

Leu Leu Phe Ala Pro Cys Ile
 1               5

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:10:
```

```
Leu Leu Phe Arg Pro Cys Ile
1               5
```

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:11:

```
Leu Leu Phe Ile Pro Cys Ile
1               5
```

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:12:

```
Leu Leu Phe Asp Pro Cys Ile
1               5
```

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:13:

```
Leu Leu Phe Trp Pro Cys Ile
1               5
```

(2) INFORMATION FOR SEQ ID NO:14:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:14:

```
Leu Leu Phe Gly Ile Cys Ile
1               5
```

(2) INFORMATION FOR SEQ ID NO:15:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 5...5
        (D) OTHER INFORMATION: where Xaa at position 5 is "pipecolic acid"

(xi) SEQUENCE DESCRIPTION: SEQ ID NO:15:

Leu Leu Phe Gly Xaa Cys Ile
1               5

(2) INFORMATION FOR SEQ ID NO:16:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: Other
            (B) LOCATION: 5...5
            (D) OTHER INFORMATION: where Xaa at position 5 is "pipecolic acid"

(xi) SEQUENCE DESCRIPTION: SEQ ID NO:16:

Tyr Phe Tyr Thr Xaa Cys Phe
1               5

(2) INFORMATION FOR SEQ ID NO:17:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:17:

Phe Val Met Ala Pro Cys Phe
1               5

(2) INFORMATION FOR SEQ ID NO:18:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:18:

Leu Leu Tyr Ser Pro Cys Phe
1               5

(2) INFORMATION FOR SEQ ID NO:19:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:19:

Ile Ser Gly Pro Cys Pro Lys
1               5

(2) INFORMATION FOR SEQ ID NO:20:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:20:

Phe Leu Phe Gly Pro Cys Ile
1               5

(2) INFORMATION FOR SEQ ID NO:21:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: Other
            (B) LOCATION: 7...7
            (D) OTHER INFORMATION: where Xaa at position 7 is "Leu-NH2"

(xi) SEQUENCE DESCRIPTION: SEQ ID NO:21:

Leu Phe Gly Pro Cys Ile Xaa
1               5

(2) INFORMATION FOR SEQ ID NO:22:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:22:

Glu Lys Gly Pro Cys Tyr Arg
1               5

(2) INFORMATION FOR SEQ ID NO:23:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:23:

Leu Leu Phe Gly Pro Cys Ile Leu
1               5

(2) INFORMATION FOR SEQ ID NO:24:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
            (A) NAME/KEY: Other
            (B) LOCATION: 8...8
            (D) OTHER INFORMATION: where Xaa at position 8 is "Leu-NH2"

(xi) SEQUENCE DESCRIPTION: SEQ ID NO:24:

Leu Leu Phe Gly Pro Cys Ile Xaa
1               5

(2) INFORMATION FOR SEQ ID NO:25:

```
    (i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 9...9
        (D) OTHER INFORMATION: where Xaa at position 9 is "Asn-NH2"

(xi) SEQUENCE DESCRIPTION: SEQ ID NO:25:

Leu Leu Phe Gly Pro Cys Ile Leu Xaa
1               5

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:26:

Leu Leu Phe Gly Pro Cys Ile Leu Asn Arg
1               5                   10

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 9...9
        (D) OTHER INFORMATION: where Xaa at position 9 is "Asn-NH2"

(xi) SEQUENCE DESCRIPTION: SEQ ID NO:27:

Phe Leu Phe Gly Pro Cys Ile Leu Xaa
1               5

(2) INFORMATION FOR SEQ ID NO:28:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 13...13
        (D) OTHER INFORMATION: where Xaa at position 13 is "Glu-NH2"

(xi) SEQUENCE DESCRIPTION: SEQ ID NO:28:

Leu Leu Phe Gly Pro Cys Ile Leu Asn Arg Leu Met Xaa
1               5                   10

(2) INFORMATION FOR SEQ ID NO:29:

(i) SEQUENCE CHARACTERISTICS:
        (A) LENGTH: 13 amino acids
        (B) TYPE: amino acid
        (D) TOPOLOGY: linear
```

(ii) MOLECULE TYPE: peptide (ix) FEATURE:
            (A) NAME/KEY: Other
            (B) LOCATION: 13...13
            (D) OTHER INFORMATION: where Xaa at position 13 is "Glu-NH2"

(xi) SEQUENCE DESCRIPTION: SEQ ID NO:29:

Phe Leu Phe Gly Pro Cys Ile Leu Asn Arg Leu Met Xaa
1               5                   10

(2) INFORMATION FOR SEQ ID NO:30:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:30:

Phe Cys Leu Gly Pro Cys Pro
1               5

(2) INFORMATION FOR SEQ ID NO:31:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:31:

Phe Cys Leu Gly Pro Cys Pro
1               5

(2) INFORMATION FOR SEQ ID NO:32:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (xi) SEQUENCE DESCRIPTION: SEQ ID NO:32:

Trp Pro Cys Gly
1

(2) INFORMATION FOR SEQ ID NO:33:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:33:

Ala Val Trp Thr Pro Cys Tyr
1               5

(2) INFORMATION FOR SEQ ID NO:34:

(i) SEQUENCE CHARACTERISTICS:
            (A) LENGTH: 8 amino acids
            (B) TYPE: amino acid (D) TOPOLOGY: linear (ii) MOLECULE TYPE: peptide (xi) SEQUENCE DESCRIPTION: SEQ ID NO:34:

Leu Glu Cys Gly Pro Cys Phe Leu
1               5

(2) INFORMATION FOR SEQ ID NO:35:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:35:

Leu Cys Ala Gly Pro Cys Phe Leu
1               5

(2) INFORMATION FOR SEQ ID NO:36:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (xi) SEQUENCE DESCRIPTION: SEQ ID NO:36:

Tyr Ile Pro Cys Phe Pro Ser Ser Leu Lys Arg Leu Leu Ile
1               5                   10

(2) INFORMATION FOR SEQ ID NO:37:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (xi) SEQUENCE DESCRIPTION: SEQ ID NO:37:

Tyr Ile Pro Cys Phe Pro Ser Ser Leu Lys Arg Leu Ile
1               5                   10

(2) INFORMATION FOR SEQ ID NO:38:

(i) SEQUENCE CHARACTERISTICS:
          (A) LENGTH: 11 amino acids
          (B) TYPE: amino acid
          (D) TOPOLOGY: linear (ii) MOLECULE TYPE: peptide (xi) SEQUENCE DESCRIPTION: SEQ ID NO:38:

Ser Gly Pro Cys Pro Lys Asp Gly Gln Pro Ser
1               5                   10

(2) INFORMATION FOR SEQ ID NO:39:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:39:

```
Thr Pro Pro Thr Pro Cys Pro Ser
1               5
```

PEPTIDES WITH IMMUNOMODULATORY EFFECTS

FIELD OF THE INVENTION

The present invention relates to new peptides, a method for the preparation of said peptides and a pharmaceutical preparation containing said peptides. The peptides according to the present invention are excellent as immunomodulating agents.

BACKGROUND OF THE INVENTION

There has been a longfelt need for new safe immunomodulatory agents in the treatment of many different diseases including malignant diseases, autoimmune diseases and asthma/allergy. Present immunomodulatory agents such as Cyclosporin A and steroids, are very potent immunosuppressive agents but also present severe side effects in a dose dependent manner. New immunomodulatory agents with higher specificity for the immune system, showing less side effects will be of great benefit in the treatment of diseases with a pathological immune response as an important component in the disease process.

PRIOR ART

Signalling between cells are to a major extent mediated by oligo- or polypeptide principles, including cytokines, neuropeptides and hormones. One possible way such a signal can be transmitted may involve oxidoreductase activity mediated by thiol-disulfide interaction of cysteine residues. This type of action can induce conformational changes of proteins which ultimately may result in a signal to the cell nuclei. Thus redox systems, based on oxidised or reduced cysteines, play important roles in initiating, maintaining and/or downregulating inflammatory responses. Redox systems that are characterized today are the thioredoxin (TR)/thioredoxin reductase (TRR) system (Holmgren et al, 1989, J.Biol.Chem, 264, 13963) and similar systems like the glutaredoxin/glutathione reductase (Bushweller et al., 1992, Biochemistry, 31, 9288) and the protein disulfide isomerase (PDI) systems (Noiva and Lennarz, 1992, J.Biol.Chem., 267, 3553). The TR/TRR system and related redox systems are potent regulators of different known immunological and inflammatory parameters, like IL-2R α-chain expression (Espinoz-Adelgado et al, 1992, J.Immunol., 149, 2961), modulation of expression of IFN-γ activity (Deiss and Kimchi, 1991, Science, 252, 117), differentiation and effector function of lymphocytes (Yodoi and Uchiyama, 1992, Immunol. Today 13, 405–411), regulation of eosinophil effector functions (Balcewics et al, 1991, J. Immunol., 147, 2170), activation of glucocorticoid receptor (Grippo et al, 1985, J.Biol.Chem. 260, 93–97) and modulation of immune response during pregnancy (Clarke et al, 1991, J.Reprod.Fert., 93, 525).

The active site of TR includes a sequence with a -Cys-Gly-Pro-Cys- motif. Selected virus proteins, e.g. gene products coded from X regions of human T-cell leukaemia viruses (Shimotohno et al, 1985, P.N.A.S. 82, 302–306) and human immunoregulatory proteins may have cysteine-containing sequences which are homologous to such a -Cys-Gly-Pro-Cys- motif. We have considered that these proteins may either express oxidoreductase activity or can be substrates for such an activity or possibly act as inhibitors of such an activity.

Previously peptides based on the cysteine-rich TR active site sequence mentioned above have been produced and shown to exhibit biological activities similar to the native protein Another example of a cysteine-containing peptide with thioredoxin-like activity was obtained from hFSH-β-(81–95) (Grasso et al, 1991, Molecular and Cellular Endocrinology 78, 163).

Analogs of thymic humoral factor γ2 (ThF-γ2) for use as immunomodulatory agents in pharmaceutical compositions are described in WO, A1, 9501182 (12.01.95). This document discloses two cyclic analogs; Leu-Glu-Cys-Gly-Pro-Cys-Phe-Leu (SEQ ID NO: 34) and Leu-Cys-Ala-Gly-Pro-Cys-Phe-Leu (SEQ ID NO: 35);, which are excluded from the present invention. However, this document does not reveal the active importance of cysteine-containing sequences.

We have prepared peptides with cysteine-containing motifs, selected from virus structural proteins e.g. retroviral transmembraneous protein p15E, and human proteins involved in regulation of inflammnation, e.g. TGF-β. Peptides were then modified to get optimal immuno-regulatory properties.

OUTLINE OF THE INVENTION

We have now surprisingly found a novel group of peptides which are excellent as immunomodulators. The peptides according to the present invention comprise 4–15 amino acids and can be described by the general formula (I):

$$A\text{-}X\text{-}Y\text{-}Cys\text{-}Z\text{-}B \qquad (I)$$

wherein
X is selected from Gly, Ala, Ile, Asp, Thr, Ser, Arg or Trp;
Y is selected from Pro, pipecolic acid (hereinafter called Pec) or Ile:
Z is selected from Ile, Phe, Pro, Ala, Tyr or Gly;
A is H, a protecting group, an amino acid in either L- or D-form with or without protected sidechain-functionality and/or N-terminal protection or an amino acid sequence with or without protected sidechain-functionalities and/or N-terminal protection;
B is OH, $NH_2$, a protecting group, an amino acid in either L- or D-form with or without protected sidechain-functionality and ending with a C-terminal amide, a free carboxyl or a protecting group or an amino acid sequence with or without protected sidechain-functionalities and ending with a C-terminal amide, a free carboxyl or a protecting group; and provided that the following sequences are excluded from the formula (I):
Leu-Glu-Cys-Gly-Pro-Cys-Phe-Leu (SEQ ID NO: 34),
Leu-Cys-Ala-Gly-Pro-Cys-Phe-Leu (SEQ ID NO: 35),
Tyr-Ile-Pro-Cys-Phe-Pro-Ser-Ser-Leu-Lys-Arg-Leu-Leu-Ile (SEQ ID NO: 36),
Tyr-Ile-Pro-Cys-Phe-Pro-Ser-Ser-Leu-Lys-Arg-Leu-Ile (SEQ ID NO: 37),
Ser-Gly-Pro-Cys-Pro-Lys-Asp-Gly-Gln-Pro-Ser (SEQ ID NO: 38) and
Thr-Pro-Pro-Thr-Pro-Cys-Pro-Ser (SEQ ID NO: 39).

The length of A and B can vary, as long as the criteria concerning length and possible amino acids or other substituents are fulfilled.

The amino acids according to the present invention can be both naturally occurring amino acids and non-naturally, synthetic amino acids or amino acid analogues.

Examples of protecting groups for A are a variety of carbamates and amides of which the following protecting groups are preferred: acetyl (Ac), 9-fluorenylmethyl carbamate (Fmoc), 1-methyl-1-(4-biphenylyl)ethyl carbamate (Bpoc), trityl (Trt), allyl carbamate (Alloc) and t-butyl carbamate (Boc).

Especially preferred protecting groups for A are acetyl (Ac), 9-fluorenylmethyl carbamate (Fmoc) and t-butyl carbamate (Boc).

Examples of protecting groups for B are a variety of esters such as $C_1-C_6$ alkyl, allyl, adamantyl, benzyl, and t-butyl.

Also within the scope of the present invention are homodimers according to the formulae (II), (III) and (IV)

A-X-Y-Cys-Z-B
|
A-X-Y-Cys-Z-B                                    (II)

A-X-Y-Cys-Z-B
|         |
A-X-Y-Cys-Z-B                                    (III)

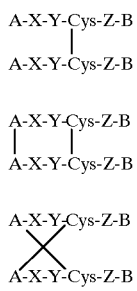
                                                 (IV)

i.e. homodimers of the peptides of the formula (I) according to the invention.

Also within the scope of the present invention are pharmaceutically acceptable salts of peptides of the formulae (I), (II), (III) and (IV).

Peptides of the formula (I) containing several cysteine residues may exist both in an oxidized and in a reduced form. The oxidized form may contain intramolecular disulfide bonds resulting in oxidized monomers or intermolecular disulfides resulting in both head to head and head to tail dimers of the peptides of formula (I).

Preferred peptides according to the present invention are peptides of the formulae (I), (II), (III) and (IV) wherein
X is Gly, Y is Pro and Z is Ile;
X is Gly, Y is Pro and Z is Gly;
X is Ala, Y is Pro and Z is Ala;
X is Ile, Y is Pro and Z is Tyr;
X is Ala, Y is Pro and Z is Ile;
X is Arg, Y is Pro and Z is Ile;
X is Ile, Y is Pro and Z is Ile;
X is Asp, Y is Pro and Z is Ile;
X is Trp, Y is Pro and Z is Ile;
X is Trp, Y is Pro and Z is Gly;
X is Gly, Y is Ile and Z is Ile;
X is Gly, Y is Pec and Z is Ile;
X is Thr, Y is Pro and Z is Tyr;
X is Thr, Y is Pec and Z is Phe;
X is Ala, Y is Pro and Z is Phe;
X is Ser, Y is Pro and Z is Phe;
X is Gly, Y is Pro and Z is Pro; or
X is Gly, Y is Pro and Z is Tyr;
wherein A and B can be varied as defined above; and provided that the following sequence is excluded from the formulae (I), (II), (III) and (IV): Ser-Gly-Pro-Cys-Pro-Lys-Asp-Gly-Gln-Pro-Ser (SEQ ID NO: 38).

Preferred peptides according to the invention are
H-Gly-Pro-Cys-Ile-OH (SEQ ID NO: 1);
Fmoc-Gly-Pro-Cys-Ile-OH (SEQ ID NO: 1);
H-Gly-Pro-Cys-Gly-OH (SEQ ID NO: 2);
H-Ala-Pro-Cys-Ala-OH (SEQ ID NO: 3);
H-Ile-Pro-Cys-Tyr-OH (SEQ ID NO: 4);
H-Trp-Pro-Cys-Gly-OH (SEQ ID NO: 32);
H-Phe-Gly-Pro-Cys-Ile-OH (SEQ ID NO: 5);
H-Gly-Pro-Cys-Ile-Leu-Asn-NH$_2$ (SEQ ID NO: 6);
H-Gly-Pro-Cys-Ile-Leu-Asn-Arg-OH (SEQ ID NO: 7);
H-Leu-Leu-Phe-Gly-Pro-Cys-Ile-OH (SEQ ID NO: 8);
H-Leu-Leu-D-Phe-Gly-Pro-Cys-Ile-OH (SEQ ID NO: 8);
H-Leu-Leu-Phe-Ala-Pro-Cys-Ile-OH (SEQ ID NO: 9);
H-Leu-Leu-Phe-Arg-Pro-Cys-Ile-OH (SEQ ID NO: 10);
H-Leu-Leu-Phe-Ile-Pro-Cys-Ile-OH (SEQ ID NO: 11);
H-Leu-Leu-Phe-Asp-Pro-Cys-Ile-OH (SEQ ID NO: 12);
H-Leu-Leu-Phe-Trp-Pro-Cys-Ile-OH (SEQ ID NO: 13);
H-Leu-Leu-Phe-Gly-Ile-Cys-Ile-OH (SEQ ID NO: 14);
H-Leu-Leu-Phe-Gly-Pec-Cys-Ile-OH (SEQ ID NO: 15);
H-Ala-Val-Trp-Thr-Pro-Cys-Tyr-OH (SEQ ID NO: 33);
H-Tyr-Phe-Tyr-Thr-Pec-Cys-Phe-OH (SEQ ID NO: 16);
H-Phe-Val-Met-Ala-Pro-Cys-Phe-OH (SEQ ID NO: 17);
H-Leu-Leu-Tyr-Ser-Pro-Cys-Phe-OH (SEQ ID NO: 18);
H-Ile-Ser-Gly-Pro-Cys-Pro-Lys-OH (SEQ ID NO: 19);
H-Phe-Leu-Phe-Gly-Pro-Cys-Ile-OH (SEQ ID NO: 20);
H-Leu-Phe-Gly-Pro-Cys-Ile-Leu-NH$_2$ (SEQ ID NO: 21);
H-Glu-Lys-Gly-Pro-Cys-Tyr-Arg-OH (SEQ ID NO: 22);
H-Leu-Leu-Phe-Gly-Pro-Cys-Ile-Leu-OH (SEQ ID NO: 23);
H-Leu-Leu-Phe-Gly-Pro-Cys-Ile-Leu-NH$_2$ (SEQ ID NO: 24);
H-Leu-Leu-Phe-Gly-Pro-Cys-Ile-Leu-OAllyl (SEQ ID NO: 23);
H-Leu-Leu-Phe-Gly-Pro-Cys-Ile-Leu-Asn-NH$_2$ (SEQ ID NO: 25);
H-Leu-Leu-Phe-Gly-Pro-Cys-Ile-Leu-Asn-Arg-OH (SEQ ID NO: 26);
H-Phe-Leu-Phe-Gly-Pro-Cys-Ile-Leu-Asn-NH$_2$ (SEQ ID NO: 27);
H-Leu-Leu-Phe-Gly-Pro-Cys-Ile-Leu-Asn-Arg-Leu-Met-Glu-NH$_2$ (SEQ ID NO: 28);
H-Phe-Leu-Phe-Gly-Pro-Cys-Ile-Leu-Asn-Arg-Leu-Met-Glu-NH$_2$ (SEQ ID NO: 29);
Fmoc-Phe-Leu-Phe-Gly-Pro-Cys-Ile-Leu-Asn-Arg-Leu-Met-Glu-NH$_2$ (SEQ ID NO: 29);
H-Phe-Cys-Leu-Gly-Pro-Cys-Pro-OH (SEQ ID NO: 30);

H-Phe-Cys-Leu-Gly-Pro-Cys-Pro-OH (SEQ ID NO:31);

H-Leu-Leu-Phe-Gly-Pro-Cys-Ile-OH
|
H-Leu-Leu-Phe-Gly-Pro-Cys-Ile-OH (homodimer of SEQ ID NO: 8);

H-Leu-Leu-Tyr-Ser-Pro-Cys-Pro-OH
|
H-Leu-Leu-Tyr-Ser-Pro-Cys-Pro-OH (homodimer of SEQ ID NO: 18);

H-Gly-Pro-Cys-Ile-OH
|
H-Gly-Pro-Cys-Ile-OH (homodimer of SEQ ID NO: 1);

H-Phe-Leu-Phe-Gly-Pro-Cys-Ile-Leu-Asn-Arg-Leu-Met-Glu-NH$_2$
|
H-Phe-Leu-Phe-Gly-Pro-Cys-Ile-Leu-Asn-Arg-Leu-Met-Glu-NH$_2$
(homodimer of SEQ ID NO: 28);

H-Phe-Cys-Leu-Gly-Pro-Cys-Pro-OH
|         |
H-Phe-Cys-Leu-Gly-Pro-Cys-Pro-OH
(head to head homodimer of SEQ ID NO: 30); and H-Phe-Cys-Leu-Gly-Pro-Cys-Pro-OH
   ╳
H-Phe-Cys-Leu-Gly-Pro-Cys-Pro-OH
(head to tail homodimer of SEQ ID NO: 30).

Especially preferred peptides according to the invention are peptides of the formulae (I), (II), (III) and (IV) wherein
X is Gly, Y is Pro and Z is Ile;
X is Ala, Y is Pro and Z is Ala;

X is Ala, Y is Pro and Z is Ile;
X is Asp, Y is Pro and Z is Ile;
X is Gly, Y is Ile and Z is Ile;
X is Gly, Y is Pec and Z is Ile;
X is Ser, Y is Pro and Z is Phe; or
X is Gly, Y is Pro and Z is Pro;
wherein A and B can be varied as defined above; and
provided that the following sequence is excluded from the formulae (I), (II), (III) and (IV): Ser-Gly-Pro-Cys-Pro-Lys-Asp-Gly-Gln-Pro-Ser (SEQ ID NO: 38).

Especially preferred peptides according to the invention are the peptides
H-Gly-Pro-Cys-Ile-OH (SEQ ID NO: 1);
H-Ala-Pro-Cys-Ala-OH (SEQ ID NO: 3);
H-Phe-Gly-Pro-Cys-Ile-OH (SEQ ID NO: 5);
H-Leu-Leu-Phe-Gly-Pro-Cys-Ile-OH (SEQ ID NO: 8);
H-Leu-Leu-Phe-Ala-Pro-Cys-Ile-OH (SEQ ID NO: 9);
H-Leu-Leu-Phe-Asp-Pro-Cys-Ile-OH (SEQ ID NO: 12);
H-Leu-Leu-Phe-Gly-Ile-Cys-Ile-OH (SEQ ID NO: 14);
H-Leu-Leu-Phe-Gly-Pec-Cys-Ile-OH (SEQ ID NO: 15);
H-Leu-Leu-Tyr-Ser-Pro-Cys-Phe-OH (SEQ ID NO: 18);
H-Leu-Leu-Phe-Gly-Pro-Cys-Ile-Leu-OH (SEQ ID NO: 23);

H-Leu-Leu-Phe-Gly-Pro-Cys-Ile-OH
|
H-Leu-Leu-Phe-Gly-Pro-Cys-Ile-OH (homodimer of SEQ ID NO: 8);
H-Leu-Leu-Tyr-Ser-Pro-Cys-Phe-OH
|
H-Leu-Leu-Tyr-Ser-Pro-Cys-Phe-OH (homodimer of SEQ ID NO: 18);
H-Phe-Cys-Leu-Gly-Pro-Cys-Pro-OH (SEQ ID NO: 30);

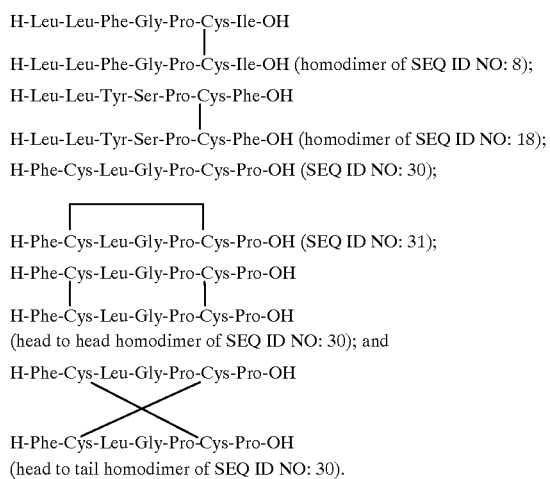

H-Phe-Cys-Leu-Gly-Pro-Cys-Pro-OH (SEQ ID NO: 31);
H-Phe-Cys-Leu-Gly-Pro-Cys-Pro-OH
|                               |
H-Phe-Cys-Leu-Gly-Pro-Cys-Pro-OH
(head to head homodimer of SEQ ID NO: 30); and
H-Phe-Cys-Leu-Gly-Pro-Cys-Pro-OH
        ⤫
H-Phe-Cys-Leu-Gly-Pro-Cys-Pro-OH
(head to tail homodimer of SEQ ID NO: 30).

The most preferred peptides according to the invention are peptides of the formulae (I), (II), (III) and (IV) wherein
X is Gly, Y is Pro and Z is Ile,
X is Ala, Y is Pro and Z is Ile;
X is Asp, Y is Pro and Z is Ile;
X is Ser, Y is Pro and Z is Phe; or
X is Gly, Y is Pro and Z is Pro;
wherein A and B can be varied as defined above; and
provided that the following sequence is excluded from the formulae (I), (II), (III) and (IV): Ser-Gly-Pro-Cys-Pro-Lys-Asp-Gly-Gln-Pro-Ser (SEQ ID NO: 38).

The most preferred peptides according to the invention are the peptides
H-Gly-Pro-Cys-Ile-OH (SEQ ID NO: 1);
H-Leu-Leu-Phe-Gly-Pro-Cys-Ile-OH (SEQ ID NO: 8);
H-Leu-Leu-Phe-Ala-Pro-Cys-Ile-OH (SEQ ID NO: 9);
H-Leu-Leu-Phe-Asp-Pro-Cys-Ile-OH (SEQ ID NO: 12);
H-Leu-Leu-Tyr-Ser-Pro-Cys-Phe-OH (SEQ ID NO: 18);
H-Leu-Leu-Phe-Gly-Pro-Cys-Ile-Leu-OH (SEQ ID NO: 23);

H-Leu-Leu-Phe-Gly-Pro-Cys-Ile-OH
|
H-Leu-Leu-Phe-Gly-Pro-Cys-Ile-OH (homodimer of SEQ ID NO: 8);
H-Leu-Leu-Tyr-Ser-Pro-Cys-Phe-OH
|
H-Leu-Leu-Tyr-Ser-Pro-Cys-Phe-OH (homodimer of SEQ ID NO: 18);
and H-Phe-Cys-Leu-Gly-Pro-Cys-Pro-OH (SEQ ID NO:31);

We have now surprisingly found that peptides of the formulae (I), (II), (III) and (IV) are excellent as immunomodulators, thus having either immunostimulating or immunoinhibitory effect. The invention thus provides peptides with advantageous properties for the treatment of diseases where an anergy of the immune response or an aberrant immune response or an ineffective host defence can be suspected. Such diseases include chronic bronchitis, where a reduction of the rate of exacerbations has previously been reported with immune response modifiers such as Biostim (Radermecker, M. et al. Int. J. Immunopharmac. 10, 913–917, 1988, Scheffer, J. et al. Arzneim Forsch/Drug Res: 41, 815–820, 1991), Ribomunyl and BronchoVaxom (Paupe, J. Respiration 58, 150–154, 1991) as well as with N-acetylcysteine (See Bergstrand, H. et al J. Free Radic. Biol. Med. 2, 119–127, 1986).

Such diseases also include certain forms of malignant diseases. Thus, numerous research institutes round the world aim at finding ways of stimulating the immune response in patients with various forms of malignant diseases and numerous reviews in the literature deal with this approach (Stevenson, F. K. FASEB J 5: 2250–2257, 1991; Melief, C. J. M. Advances in Cancer Research 58: 143–75, 1992, Chen, J. et al., Immunology Today 14:10, 483–86, 1993). To mention one example patients with intracranial tumours (gliomas) exhibit a profound decrease in immunity possibly due to a defect in the secretion of IL-2 as well as the expression of IL-2 receptors in T cells from these patients (Roszman, T. et al. Immunology Today 12, 370–374, 1991). Moreover, a significant adjuvant effect in immunotherapy of melanoma and colon carcinoma has been documented for the immunostimulator Levamisole (Van Wauwe, J. and Janssen, P. A. J: Int J. Immunopharmac 13, 3–9, 1991) and immunotherapy with IL-2 in vivo or treatment of patients lymphokine activated killer cells with IL-2 ex vivo has caused the regression of cancer in selected patients (Rosenberg, S. A. Immunology Today 9, 58–62, 1988). The malignant diseases where the peptides of the formulae (I), (II), (III) and (IV) can be expected to have advantageous effects include tumours of mesenchymal origin such as sarcomas like fibrosarcoma, myxosarcoma, liposarcoma, chondrosarcoma, osteogenic sarcoma or chordosarcoma, sarcomas like angiosarcoma, endotheliosarcoma, lymphangiosarcoma, synoviosarcoma or mesotheliosarcoma, leukemias and lymphomas like granulocytic leukemia, monocytic leukemia, lymphocytic leukemia, malignant lymphoma, plasmocytoma, reticulum cell sarcoma or Hodgkins disease, sarcomas like leiomysarcoma or rhabdomysarcoma, tumours of epithelial origin (Carcinomas) like squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma-cholangiocarcinoma, papillary carcinoma, transitional cell carcinoma, squamous cell carcinoma, choriocarcinoma, semonoma or embryonal carcinoma, tumours of the central nervous system like glioma, meningoma, medulloblastoma, schwannoma or ependymoma.

Moreover, the peptides according to the present invention also have advantageous properties for the treatment of chronic infections such as herpes, aphtous stomatitis and minimal change syndrome where clinical improvement has previously been reported by treatment with an immunostimulator such as Levamisole as well as other chronic inflammatory diseases in the urinary tract or in ear, nose or throut, which benefit from treatment with immunostimulators such as Biostim, Broncho-Vaxom and Ribomunyl, or at HIV infection or AIDS.

Moreover, an impairment, a defect or an imbalance of the immune response has also been postulated to exist at atopic diseases such as atopic dermatitis, rhinitis and asthma (Katz, D. H. Immunology Rewiews 41, 77–108, 1977). Since theoretical considerations suggest that stimulation of an immune response would possibly be the best way of restoring imbalances and autoimmunity (Varela, F. J. and Coutinho, A. Immunology Today 12, 159–166, 1991), the peptides can also be expected to have advantageous properties for the treatment of asthma, rhinitis, atopic dermatitis and autoimmune diseases like non-obese diabetes, systemic lupus erythematosus, sclerodermia, Sjögren's syndrome, dermatomyositis or multiple sclerosis, rheumatoid arthritis and possibly psoriasis.

Moreover, the peptides according to the present invention, due to their immune modulating properties, may have advantageous properties as adjuvants in various forms of vaccine preparations. Due to their immune modulating properties, the peptides can also be expected to have favourable properties in inhibiting rejection of organs/transplants.

Finally, the peptides according to the present invention can be expected to have advantageous properties in the treatment of artheriosclerosis, whether or not they will influence a putative inflammatory process in this condition (Hansson. G. K. et al. Proc. Nat. Acad. Sci. USA 88, 10530, 1991).

The peptides according to the present invention are particulary suitable for treatment of malignancies such as melanoma, mammary carcinoma, gastrointestinal carcinoma, glioma, bladder carcinoma and squamous cell carcinoma of the neck and head region; infections such as chronic bronchitis, hepatitis, post-infectious anergy and aquired immune deficiencies such as AIDS; posttraumatic immunological anergy; and purported autoimmune diseases such as rheumatoid arthritis, multiple sclerosis, artheriosclerosis and psoriasis.

Preparation

The peptides according to the present invention may be prepared using the standard solid phase sequential coupling technique utilizing an automatic peptide synthesizer (see for example: Jones, J. The Chemical Synthesis of Peptides, pp 132–156, first edition, Oxford University Press, 1991 and R. Epton (ed) Innovation and Perspectives in Solid Phase Synthesis, SPCC (UK) Ltd, 1990). The preparation starts form the C-terminal amino acid which can be obtained grafted to a methylbenzhydrylamine, benzhydrylamine or chloromethylated resin or other suitable solid support. The other amino acids are grafted step by step, after having protected the side chains thereof. In this coupling method the α-amino groups of the amino acids are protected either with Fmoc or t-Boc methodology.

Protective groups for the side chains of amino acids are well known in the art. The whole protected peptide is released either from the chloromethylated resin by ammoniolysis to obtain the protected amide, or from the methylbenzhydrylamine or benzhydrylamine resins by acidolysis.

Peptides according to the invention may also be prepared using solution methods, by either stepwise or fragment condensations (see for example: Jones, J. The Chemical Synthesis of Peptides, pp 115–131, first edition, Oxford University Press, 1991). An appropriately alpha aminoprotected amino acid is coupled to an appropriately alpha carboxyl protected amino acid (such protection may not be required depending on the coupling method chosen) using diimides, symmetrical or unsymmetrical anhydrides, or other coupling reagents or techniques known to those skilled in the art. These techniques may be either chemical or enzymatic. The alpha amino and/or alpha carboxyl protecting groups are removed and the next suitably protected amino acid or block of amino acids are coupled to extend the growing peptide. Various combinations of protecting groups and of chemical and/or enzymatic techniques and assembly strategies can be used in each synthesis.

The dimers (peptides of the formulae (II), (III) and (IV)) and peptides containing intramolecular disulfide bonds between cysteine residues may be prepared via general oxidation techniques described by Andreu et al in Methods in Molecular Biology, Peptide Synthesis Protocols vol 35 (Humana Press Inc., Totowa, N.J., 1994) and Ruiz-Gayo et al, 1988, Tetrahedron Letters, 29, 3845–3848, as well as in other reference works known to those skilled in the art. Low-resolution mass spectra and accurate mass determinations were recorded on an Autospec-Q, Fisons Analytical, double focusing sector instrument equiped with a LSIMS interface.

DETAILED DESCRIPTION OF THE INVENTION

The invention will now be described in more detail with the following examples which are not to be construed as limiting the invention.

EXAMPLE 1

Synthesis of H-Gly-Pro-Cys-Ile-OH (SEQ ID NO: 1)

A resin (0.37 g, 0.22 mequiv/g, 81 μmol) consisting of a crosslinked polystyrene backbone grafted with polyethyleneglycol chains, functionalized with the linker p-hydroxymethylphenoxyacetic acid (Sheppard and Williams, 1982, Int. J. Peptide Protein Res., 20, 451–454) and Fmoc-Ile, from Rapp Polymere (Germany) was used for the synthesis. $N^\alpha$-Fmoc amino acids were from Bachem (Switzerland), and Cys was protected with a triphenylmethyl (Trt) group. DMF was distilled before being used.

The $N^\alpha$-Fmoc amino acids were coupled to the peptide-resin as 7-aza-1-benzotriazolyl (HOAt) esters (Carpino, 1993, J. Am. Chem. Soc. 115, 4397–4398). These were prepared, in situ, in the peptide synthesizer from the appropriate $N^\alpha$-Fmoc amino acid (0.32 mmol) and HOAt (65 mg, 0.48 mmol) by addition of DMF (0.5 ml) and a solution of 1,3-diisopropyl-carbodiimide in DMF (0.39 M, 0.8 ml, 0.312 mmol). After 45 min bromophenol blue (Flegel and Sheppard, 1990, J. Chem. Soc., Chem. Commun. 536–538) in DMF (0.15mM, 0.4 ml) was added to the HOAt ester by the synthesizer, and the resulting solution was recirculated through the column. The acylation was monitored (Flegel and Sheppard, 1990, J. Chem. Soc., Chem. Commun. 536–538) using the absorbance of bromophenol blue at 600 nm, and when the coupling was complete the peptide-resin was automatically washed with DMF. Coupling times for different $N^\alpha$-Fmoc amino acids were approximately 30 min.

N$^\alpha$-Fmoc deprotection of the peptide resin was performed by a flow of 20% piperidine in DMF through the column for 12.5 min, and was monitored (Dryland and Sheppard, 1986, J. Chem. Soc. Perkin Trans. I, 125–137) using the absorbance of the dibenzofulvene-piperidine adduct at 350 nm. After completion of the N$^\alpha$-Fmoc deprotection the peptide-resin was again washed automatically with DMF.

After completion of the synthesis and cleavage of the N-terminal N$^\alpha$-Fmoc group, the resin was washed with dichloromethane (5×5 ml) and dried under vacuum. The peptide (40 μmol) was then cleaved from the resin (200 mg), and the amino acid side chains were deprotected, by treatment with trifluoroacetic acid-water-thioanisole-ethanedithiol (87.5:5 5:5:2.5, 20 ml) for 2 h, followed by filtration. Acetic acid (20 ml) was added to the filtrate, the solution was concentrated, and acetic acid (20 ml) was added again before the solution was concentrated. The residue was dissolved in acetic acid-water (4:1, 25 ml) and the solution was freeze dried. The residue was triturated with ether (10 ml) which gave a solid, crude peptide (21 mg) after drying under vacuum.

The peptide was analyzed on a Beckman System Gold HPLC using a Kromasil C-8 column (1000 Å, 4.6×250 mm) and a linear gradient of 0–80% of B in A over 60 min with a flow rate of 1.5 ml/min and detection at 214 nm (solvent systems A: 0.1% aqueous trifluoroacetic acid and B: 0.1% trifluoroacetic acid in acetonitrile). Purification of the crude peptide (21 mg) was performed with the same HPLC system on a 20×250 mm Kromasil C-8 column with a flow rate of 11 ml/min and gave pure a product (8.5 mg, 55%). FAB-MS: 389 (MH$^+$).

The compound is also listed in table 1.

EXAMPLES 2–33

The peptides according to examples 2–33 were prepared using the same protocol as in example 1.

The compounds are listed in table 1.

EXAMPLE 34

Synthesis of H-Leu-Leu-Phe-Gly-Pro-Cys-Ile-OH
|
H-Leu-Leu-Phe-Gly-Pro-Cys-Ile-OH
(homodimer of SEQ ID NO: 8)

A solution of the monomer (1.5 mg/ml, in 50 nM phosphate buffer, pH=7.2) containing 5 ppm copper(II)-sulphate was stirred at room temperature for 20 hours. The solution was lyophilized and redissolved in water/acetonitrile (80/20) and purified by reverse phase HPLC using a VYDAC C-18 column (5 μm, 4×250 mm). An aqueous solution containing 0.1% trifluoroacetic acid and 5% acetonitrile was used as a mobile phase. The concentration of acetonitrile was increased linearly to 60% over a time scale of 25 min. The flow rate was 1.5 ml/min and the components were detected with UV at 220 nm. Fractions were collected manually and checked with FAB-MS. Repeated injections were pooled to give a solution of the product which was lyophilized. FAB-MS: 1521 (MH$^+$).

The compound is listed in table 1.

EXAMPLES 35–37

The peptides according to examples 35–37 were prepared using the same protocol as in example 34.

The compounds are listed in table 1.

EXAMPLE 38

The peptide according to example 38 was prepared using the same protocol as in example 1.

The compound is listed in table 1.

EXAMPLE 39

The peptide according to example 39 was prepared using the same protocol as in example 34–37.

The compounds are listed in table 1.

EXAMPLES 40–41

The peptides according to examples 40–41 were prepared using the same protocol as in example 1.

The compounds are listed in table 1.

EXAMPLE 42

Synthesis of H-Phe-Cys-Leu-Gly-Pro-Cys-Pro-OH
|                                    |
H-Phe-Cys-Leu-Gly-Pro-Cys-Pro-OH
(head to head homodimer of SEQ ID NO: 30)

To prepare the parallel (head to head) homodimer a single peptide chain with an Acm (acetamidomethyl) protecting group on one of the cysteines and with the other cysteine unprotected (H-Phe-Cys-Leu-Gly-Pro-Cys(Acm)-Pro-OH) was synthesized using the same protocol as in example 1. The monomer was dimerized through oxidation of the free cysteines using the same protocol as in example 2. The second disulfide bond was accomplished using the protocol of Ruiz-Gayo (Ruiz-Gayo et al, 1988, Tetrahedron Letters, 29, 3845–3848) in which a onepot deprotection and oxidation of the Acm protected cysteine with iodine in 80% aqueous acetic acid resulted in a crude product which was purified on HPLC.

The compound is listed in table 1.

EXAMPLE 43

Synthesis of H-Phe-Cys-Leu-Gly-Pro-Cys-Pro-OH
                       ╲     ╱
H-Phe-Cys-Leu-Gly-Pro-Cys-Pro-OH
(head to tail homodimer of SEQ ID NO: 30)

To prepare the antiparallel (head to tail) homodimer the general procedure of Ruiz-Gayo was used (Ruiz-Gayo et al, 1988, Tetrahedron Letters, 29, 3845–3848). Two single peptide chains each with an Acm (acetamidomethyl) protecting group on one of the cysteines and with the other cysteine unprotected (H-Phe-Cys-Leu-Gly-Pro-Cys(Acm)-Pro-OH and H-Phe-Cys(Acm)-Leu-Gly-Pro-Cys-Pro-OH) was synthesized using the same protocol as in example 1. The unprotected cysteines on one of the monomers was activated with dithiopyridine resulting in the S-pyridyl derivative H-Phe-Cys(SPyr)-Leu-Gly-Pro-Cys(Acm)-Pro-OH. This derivative was reacted with the second peptide chain resulting in the first disulfide. The second disulfidebond was accomplished using the same protocol as in example 42 with iodine in 80% aqueous acetic acid which, after purification on HPLC, resulted in the final product.

The compound is listed in table 1.

The following Table 1 lists compounds according to the invention and their identification by FAB-MS spectra.

TABLE 1

| Ex. No. | Peptide | MH+(m/z) |
|---|---|---|
| 1 | H-Gly-Pro-Cys-Ile-OH (SEQ ID NO: 1) | 389 |
| 2 | Fmoc-Gly-Pro-Cys-Ile-OH (SEQ ID NO: 1) | 611 |
| 3 | H-Gly-Pro-Cys-Gly-OH (SEQ ID NO: 2) | 333 |
| 4 | H-Ala-Pro-Cys-Ala-OH (SEQ ID NO: 3) | 361 |
| 5 | H-Ile-Pro-Cys-Tyr-OH (SEQ ID NO: 4) | 495 |
| 6 | H-Trp-Pro-Cys-Gly-OH (SEQ ID NO: 32) | 462 |
| 7 | H-Phe-Gly-Pro-Cys-Ile-OH (SEQ ID NO: 5) | 537 |
| 8 | H-Gly-Pro-Cys-Ile-Leu-Asn-NH$_2$ (SEQ ID NO: 6) | calcd: 615.329 (Exact miss) found: 615.329 |
| 9 | H-Leu-Leu-Phe-Gly-Pro-Cys-Ile-OH (SEQ ID NO: 8) | calcd: 762.422 (Exact mass) found: 762.419 |
| 10 | H-Leu-Leu-Phe-Gly-Pro-Cys-Ile-OH (SEQ ID NO:8) | 762 |
| 11 | H-Leu-Leu-Phe-Ala-Pro-Cys-Ile-OH (SEQ ID NO: 9) | calcd: 776.438 (Exact mass) found: 776.438 |
| 12 | H-Leu-Leu-Phe-Arg-Pro-Cys-Ile-OH (SEQ ID NO: 10) | 861 |
| 13 | H-Leu-Leu-Phe-Ile-Pro-Cys-Ile-OH (SEQ ID NO: 11) | 808 |
| 14 | H-Leu-Leu-Phe-Asp-Pro-Cys-Ile-OH (SEQ ID NO: 12) | 819 |
| 15 | H-Leu-Leu-Phe-Trp-Pro-Cys-Ile-OH (SEQ ID NO: 13) | 891 |
| 16 | H-Leu-Leu-Phe-Gly-Ile-Cys-Ile-OH (SEQ ID NO: 14) | 778 |
| 17 | H-Leu-Leu-Phe-Gly-Pec-Cys-Ile-OH (SEQ ID NO: 15) | calcd: 776.438 (Exact mass) found: 776.439 |
| 18 | H-Ala-Val-Trp-Thr-Pro-Cys-Tyr-OH (SEQ ID NO: 33) | 839 |
| 19 | H-Tyr-Phe-Tyr-Thr-Pec-Cys-Phe-OH (SEQ ID NO: 16) | 954 |
| 20 | H-Phe-Val-Met-Ala-Pro-Cys-Phe-OH (SEQ ID NO: 17) | 814 |
| 21 | H-Leu-Leu-Tyr-Ser-Pro-Cys-Phe-OH (SEQ ID NO: 18) | 842 |
| 22 | H-Ile-Ser-Gly-Pro-Cys-Pro-Lys-OH (SEQ ID NO: 19) | calcd: 701.384 (Exact mass) found: 701.386 |
| 23 | H-Phe-Leu-Phe-Gly-Pro-Cys-Ile-OH (SEQ ID NO: 20) | 796 |
| 24 | H-Leu-Phe-Gly-Pro-Cys-Ile-Leu-NH$_2$ (SEQ ID NO: 21) | calcd: 761.438 (Exact mass) found: 761.437 |
| 25 | H-Glu-Lys-Gly-Pro-Cys-Tyr-Arg-OH (SEQ ID NO: 22) | 852 |
| 26 | H-Leu-Leu-Phe-Gly-Pro-Cys-Ile-Leu-OH (SEQ ID NO: 23) | 875 |
| 27 | H-Leu-Leu-Phe-Gly-Pro-Cys-Ile-Leu-NH$_2$ (SEQ ID NO: 24) | 878 |
| 28 | H-Leu-Leu-Phe-Gly-Pro-Cys-Ile-Leu-OAllyl (SEQ ID NO: 23) | 915.5 |
| 29 | H-Leu-Leu-Phe-Gly-Pro-Cys-Ile-Leu-Asn-NH$_2$ (SEQ ID NO: 25) | 988 |
| 30 | H-Phe-Leu-Phe-Gly-Pro-Cys-Ile-Leu-Asn-NH$_2$ (SEQ ID NO: 27) | calcd: 1022.550 (Exact mass) found: 1022.551 |
| 31 | H-Leu-Leu-Phe-Gly-Pro-Cys-Ile-Leu-Asn-Arg-Leu-Met-Glu-NH$_2$ (SEQ ID NO: 28) | 1517 |
| 32 | H-Phe-Leu-Phe-Gly-Pro-Cys-Ile-Leu-Asn-Arg-Leu-Met-Glu-NH$_2$ (SEQ ID NO: 29) | 1552 |
| 33 | Fmoc-Phe-Leu-Phe-Gly-Pro-Cys-Ile-Leu-Asn-Arg-Leu-Met-Glu-NH$_2$ (SEQ ID NO: 29) | 1776 |
| 34 | H-Leu-Leu-Phe-Gly-Pro-Cys-Ile-OH \| H-Leu-Leu-Phe-Gly-Pro-Cys-Ile-OH (homodimer of SEQ ID NO: 8) | 1521 |
| 35 | H-Leu-Leu-Tyr-Ser-Pro-Cys-Phe-OH \| H-Leu-Leu-Tyr-Ser-Pro-Cys-Phe-OH (homodimer of SEQ ID NO: 18) | 1682 |
| 36 | H-Gly-Pro-Cys-Ile-OH \| H-Gly-Pro-Cys-Ile-OH (homodimer of SEQ ID NO: 1) | 775 |
| 37 | H-Phe-Leu-Phe-Gly-Pro-Cys-Ile-Leu-Asn-Arg-Leu-Met-Glu-NH$_2$ \| H-Phe-Leu-Phe-Gly-Pro-Cys-Ile-Leu-Asn-Arg-Leu-Met-Glu-NH$_2$ (homodimer of SEQ ID NO: 29) | 3101 |
| 38 | H-Phe-Cys-Leu-Gly-Pro-Cys-Pro-OH (SEQ ID NO: 30) | 736 |
| 39 | H-Phe-Cys-Leu-Gly-Pro-Cys-Pro-OH (SEQ ID NO: 31) | 734 |
| 40 | H-Gly-Pro-Cys-Ile-Leu-Asn-Arg-OH (SEQ ID NO: 7) | 772 |
| 41 | H-Leu-Leu-Phe-Gly-Pro-Cys-Ile-Leu-Asn-Arg-OH (SEQ ID NO: 26) | 1146 |
| 42 | H-Phe-Cys-Leu-Gly-Pro-Cys-Pro-OH \| H-Phe-Cys-Leu-Gly-Pro-Cys-Pro-OH (head to head homodimer of SEQ ID NO: 30) | 1467.7 |
| 43 | H-Phe-Cys-Leu-Gly-Pro-Cys-Pro-OH ⨯ H-Phe-Cys-Leu-Gly-Pro-Cys-Pro-OH (head to tail homodimer of SEQ ID NO: 30) | 1468 |

Pharmaceutical Preparations

The peptides according to the invention may be administered orally, nasally, rectally, intravenously or by inhalation.

The dosage will depend on the route of administration, the severity of the disease, age and weight of the patient and other factors normally considered by the attending physician, when determining the individual regimen and dosage level as the most appropriate for a particular patient.

The pharmaceutical preparations comprising the peptides according to the invention may conveniently be tablets, pills, capsules, syrups, powders or granules for oral administration sterile parenteral solutions or suspensions for parenteral administration or suppositories for rectal administration.

For the preparation of pharmaceutical preparations containing a peptide according to the present invention in the form of dosage units for oral administration, the active peptide may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a polymer known to the man skilled in the art, dissolved in a readily volatile organic solvent or mixture of organic solvents. Dyestuffs may be added to these coatings in order to readily distinguish between tablets containing different active substances or different amounts of the active peptides.

For the preparation of soft gelatine capsules, the active substance may be admixed with e.g. a vegetable oil or polyethylene glycol. Hard gelatine capsules may contain granules of the active substance using either the above mentioned excipients for tablets, e.g. lactose, saccharose, sorbitol, mannitol, starches (e.g. potato starch, corn starch or amylopectin), cellulose derivatives or gelatine. Also liquids or semisolids of the drug may be filled into hard gelatine capsules.

Dosage units for rectal application may be solutions or suspensions, or may be prepared in the form of suppositories comprising the active substance in admixture with a neutral fatty base, or gelatin rectal capsules comprising the active substance in admixture with vegetable oil or paraffin oil.

Liquid preparations for oral application may be in the form of syrups or suspensions, for example solutions containing a peptide as herein described as the active substance, the balance being sugar and a mixture of ethanol, water, glycerol and propylene glycol. Optionally such liquid preparations may contain colouring agents, flavouring agents, saccharine and carboxymethylcellulose as a thickening agent or other excipients known to the skilled man in art.

Solutions for parenteral applications by injection may be prepared in an aqueous solution of a water-soluble pharmaceutically acceptable salt of the active substance. These solutions may also contain stabilizing agents and/or buffering agents and may involve the use of surface acting agents to improve solubility. They may conveniently be provided in various dosage unit ampoules.

The compounds according to the invention may be formulated in pressurised metered dose inhalers or dry powder inhalers for oral or nasal inhalation or in liquid formulations for nebulisation. The active substance is micronised or otherwise processed to a particle size suitable for inhalation therapy (mass median diameter <4 $\mu$m).

For pressurised metered dose inhalers the micronized substance is suspended in a liquefied propellant or a mixture of liquefied propellants which also can act as solvents and filled into a container which is equipped with a metering valve.

The propellants used may be hydrofluoroalkanes (HFAs) of different compositions. The most frequent used HFAs are tetrafluoroethane (propellant 134a) and heptafluoropropane (propellant 227).

Low concentrations of surfactants such as sorbitan trioleate, lecithin, oleic acid or other suitable substances may be used to improve the physical stability of the preparation. Ethanol or other solvents may be used to increase the solubility of the substances in the propellants.

The active substance may also be delivered through a portable inhaler device suitable for dry powder inhalation. The active substance may be used alone or be combined with a suitable carrier substance such as lactose, mannitol or glucose. Other additives may also be included in the powder formulation by various reasons, such as to increase the stability. The inhaler may be a single dose inhaler with one predispensed dose or a multi dose inhaler in which the dose is created by a metering unit within the inhaler or is delivered from an assembly of predispensed doses.

Biological Studies

The ability of the peptides according to the invention to modulate immune responses can be illustrated by its efficacy in the animal delayed type hypersensitivity (DTH) test in mice.

Both male and female Balb/c mice, obtained from Bomholtsgaard (Denmark), were used with a weight of 18–20 gram.

4-Ethoxymethylene-2-phenyloxazolin-5-one (OXA) (England) and served as the antigen in this test.

The mice were sensitized, Day 0, by epicutaneous application of 150 $\mu$l of an absolute ethanol-acetone (3:1) solution containing 3% OXA on the shaved abdomen. Treatment with the peptide or vehicle (0.9% NaCl) was initiated by oral feeding immediately after sensitization an continued once daily until Day 6. Seven days (Day 6) after the sensitization, both ears of all mice were challenged on both sides by topical application of 20 $\mu$l 1% OXA dissolved in peanut oil. Ear thickness was measured prior to and 24 or 48 hours after challenge using an Oditest spring calliper. Challenges and measurements were performed under light pentobarbital anaesthesia.

The intensity of the DTH reactions was expressed according to the formula: $T_{t24/48} - T_{t0}$ $\mu$m units, where t0, t24 and t48 represent the ear thickness before and 24 or 48 hours after challenge respectively, in individual tests (T). The result were expressed as the mean ±S.E.M. The level of significance between means of the groups was obtained by Student's two-tailed t-test. The immunomodulating effect of the peptide is reflected in a significant difference in the increase or decrease in ear thickness as compared to the control.

DISCUSSION

The present invention describes peptides that can be expected to have favorable effects for the treatment of various diseases, affecting the immune system including diseases where an anergy of the immune response, an aberrant immune response or peripheral tolerance to pathogenes or an ineffective host defence by other reasons can be suspected. These type of drugs have an urgent need on the market, instead of or as a complement to present more toxic drugs, for the treatment of many diseases.

| Abbreviations | |
|---|---|
| Pec | pipecolic acid |
| Ac | acetyl |
| Fmoc | 9-fluorenylmethyl carbamate |
| Bpoc | 1-methyl-1-(4-biphenylyl)ethyl carbamate |
| Trt | trityl |
| Alloc | allyl carbamate |
| Boc | t-butyl carbamate |
| FAB-MS | fast atom bombardment mass spectrometry |
| DTH | delayed type hypersensitivity |
| OXA | 4-ethoxymethylene-2-phenyloxazolin-5-one |
| Acm | acetamidomethyl |

We claim:

1. A homodimer of a peptide comprising 4–15 amino acids according to Formula II:

$$\begin{array}{c} \text{A-X-Y-Cys-Z-B} \\ | \\ \text{A-X-Y-Cys-Z-B} \end{array} \quad (II)$$

wherein
X is Gly, Y is Pro and Z is Ile;
X is Gly, Y is Pro and Z is Gly;
X is Ala, Y is Pro and Z is Ala;
X is Ile, Y is Pro and Z is Tyr;
X is Ala, Y is Pro and Z is Ile;
X is Arg, Y is Pro and Z is Ile;
X is Ile, Y is Pro and Z is Ile;
X is Asp, Y is Pro and Z is Ile;
X is Trp, Y is Pro and Z is Ile;
X is Trp, Y is Pro and Z is Gly;
X is Gly, Y is Ile and Z is Ile;
X is Gly, Y is Pec and Z is Ile;
X is Thr, Y is Pro and Z is Tyr;
X is Thr, Y is Pec and Z is Phe;
X is Ala, Y is Pro and Z is Phe;
X is Ser, Y is Pro and Z is Phe;
X is Gly, Y is Pro and Z is Pro; or
X is Gly, Y is Pro and Z is Tyr; and
A is H, an N-terminal protecting group, or at least one amino acid in either L-form or D-form, with or without protected side chain-functionality and with or without N-terminal protection; and
B is OH, NH$_2$, a C-terminal protecting group, or at least one amino acid in either L-form or D-form, with or without protected side chain-functionality and ending with a C-terminal amide, a free carboxyl group, or a protecting group;
provided a homodimer of the peptide Pro-Cys-Pro-Lys-Asp-Gly-Gln-Pro-Ser (SEQ ID NO:38) is excepted from Formula II.

2. The homodimer of claim 1, wherein
X is Gly, Y is Pro and Z is Ile;
X is Ala, Y is Pro and Z is Ile;
X is Arg, Y is Pro and Z is Ile;
X is Asp, Y is Pro and Z is Ile;
X is Trp, Y is Pro and Z is Ile;
X is Ser, Y is Pro and Z is Phe; or
X is Gly, Y is Pro and Z is Pro.

3. The homodimer of claim 1, wherein
A is H, an N-terminal protecting group, an amino acid in either L-form or D-form selected from the group consisting of Phe, Leu, Met, Ser, Lys and Tyr, with or without protected side chain-functionality and with or without an N-terminal protecting group, or an amino acid sequence having Phe, Leu, Met, Ser, Lys or Tyr as the most C-terminal amino acid in the sequence, with or without protected side chain-functionalities and with or without an N-terminal protecting group, wherein the N-terminal protecting group is selected from the group consisting of an acetyl group (Ac), a 9-fluorenylmethyl carbamate group (Fmoc), a 1-methyl-1-(4-biphenylyl) ethyl carbamate group (Bpoc), a trityl group (Trt), an allyl carbamate group (Alloc) and a t-butyl carbamate group (Boc); and
B is OH, NH$_2$, a C-terminal protecting group, an amino acid in either L-form or D-form selected from the group consisting of Leu, Lys or Arg, with or without protected sidechain-functionality and ending with a C-terminal amide, a free carboxyl group, or a C-terminal protecting group, or an amino acid sequence having Leu, Lys or Arg, as the most N-terminal amino acid of the sequence, with or without protected sidechain-functionalities and ending with a C-terminal amide, a free carboxyl group, or a C-terminal protecting group, wherein the C-terminal protecting group is selected from the group consisting of a C$_1$–C$_6$ alkyl group, an allyl group, an adamantyl group, a benzyl group, and a t-butyl group;
provided a homodimer of the peptide Pro-Cys-Pro-Lys-Asp-Gly-Gln-Pro-Ser (SEQ ID NO:38) is excepted from Formula II.

4. A homodimer selected from the group consisting of

```
H-Gly-Pro-Cys-Ile-OH
        |
H-Gly-Pro-Cys-Ile-OH                    (homodimer of SEQ ID NO:1);

Fmoc-Gly-Pro-Cys-Ile-OH
        |
Fmoc-Gly-Pro-Cys-Ile-OH                 (homodimer of SEQ ID NO:1);

H-Gly-Pro-Cys-Gly-OH
        |
H-Gly-Pro-Cys-Gly-OH                    (homodimer of SEQ ID NO:2);

H-Ala-Pro-Cys-Ala-OH
        |
H-Ala-Pro-Cys-Ala-OH                    (homodimer of SEQ ID NO:3);
```

-continued

```
H-Ile-Pro-Cys-Tyr-OH
           |
H-Ile-Pro-Cys-Tyr-OH                          (homodimer of SEQ ID NO:4);

H-Trp-Pro-Cys-Gly-OH
           |
H-Trp-Pro-Cys-Gly-OH                          (homodimer of SEQ ID NO:32);

H-Phe-Gly-Pro-Cys-Ile-OH
               |
H-Phe-Gly-Pro-Cys-Ile-OH                      (homodimer of SEQ ID NO:5);

H-Gly-Pro-Cys-Ile-Leu-Asn-NH₂
           |
H-Gly-Pro-Cys-Ile-Leu-Asn-NH₂                 (homodimer of SEQ ID NO:6);

H-Gly-Pro-Cys-Ile-Leu-Asn-Arg-NH₂
           |
H-Gly-Pro-Cys-Ile-Leu-Asn-Arg-NH₂             (homodimer of SEQ ID NO:7);

H-Leu-Leu-Phe-Gly-Pro-Cys-Ile-OH
                       |
H-Leu-Leu-Phe-Gly-Pro-Cys-Ile-OH              (homodimer of SEQ ID NO:8);

H-Leu-Leu-D-Phe-Gly-Pro-Cys-Ile-OH
                         |
H-Leu-Leu-D-Phe-Gly-Pro-Cys-Ile-OH            (homodimer of SEQ ID NO:8);

H-Leu-Leu-Phe-Ala-Pro-Cys-Ile-OH
                       |
H-Leu-Leu-Phe-Ala-Pro-Cys-Ile-OH              (homodimer of SEQ ID NO:9);

H-Leu-Leu-Phe-Arg-Pro-Cys-Ile-OH
                       |
H-Leu-Leu-Phe-Arg-Pro-Cys-Ile-OH              (homodimer of SEQ ID NO:10);

H-Leu-Leu-Phe-Ile-Pro-Cys-Ile-OH
                       |
H-Leu-Leu-Phe-Ile-Pro-Cys-Ile-OH              (homodimer of SEQ ID NO:11);

H-Leu-Leu-Phe-Asp-Pro-Cys-Ile-OH
                       |
H-Leu-Leu-Phe-Asp-Pro-Cys-Ile-OH              (homodimer of SEQ ID NO:12);

H-Leu-Leu-Phe-Trp-Pro-Cys-Ile-OH
                       |
H-Leu-Leu-Phe-Trp-Pro-Cys-Ile-OH              (homodimer of SEQ ID NO:13);

H-Leu-Leu-Phe-Gly-Ile-Cys-Ile-OH
                       |
H-Leu-Leu-Phe-Gly-Ile-Cys-Ile-OH              (homodimer of SEQ ID NO:14);

H-Leu-Leu-Phe-Gly-Pec-Cys-Ile-OH
                       |
H-Leu-Leu-Phe-Gly-Pec-Cys-Ile-OH              (homodimer of SEQ ID NO:15);

H-Ala-Val-Trp-Thr-Pro-Cys-Tyr-OH
                       |
H-Ala-Val-Trp-Thr-Pro-Cys-Tyr-OH              (homodimer of SEQ ID NO:33);

H-Tyr-Phe-Tyr-Thr-Pec-Cys-Phe-OH
                       |
H-Tyr-Phe-Tyr-Thr-Pec-Cys-Phe-OH              (homodimer of SEQ ID NO:16);

H-Phe-Val-Met-Ala-Pro-Cys-Phe-OH
                       |
H-Phe-Val-Met-Ala-Pro-Cys-Phe-OH              (homodimer of SEQ ID NO:17);

H-Leu-Leu-Tyr-Ser-Pro-Cys-Phe-OH
                       |
H-Leu-Leu-Tyr-Ser-Pro-Cys-Phe-OH              (homodimer of SEQ ID NO:18);

H-Ile-Ser-Gly-Pro-Cys-Pro-Lys
                   |
H-Ile-Ser-Gly-Pro-Cys-Pro-Lys-OH              (homodimer of SEQ ID NO:19);

H-Phe-Leu-Phe-Gly-Pro-Cys-Ile-OH
                       |
H-Phe-Leu-Phe-Gly-Pro-Cys-Ile-OH              (homodimer of SEQ ID NO:20);
```

-continued

```
H-Leu-Phe-Gly-Pro-Cys-Ile-Leu-NH₂
                  |
H-Leu-Phe-Gly-Pro-Cys-Ile-Leu-NH₂                          (homodimer of SEQ ID NO:21);

H-Glu-Lys-Gly-Pro-Cys-Tyr-Arg-OH
                  |
H-Glu-Lys-Gly-Pro-Cys-Tyr-Arg-OH                           (homodimer of SEQ ID NO:22);

H-Leu-Leu-Phe-Gly-Pro-Cys-Ile-Leu-OH
                      |
H-Leu-Leu-Phe-Gly-Pro-Cys-Ile-Leu-OH                       (homodimer of SEQ ID NO:23);

H-Leu-Leu-Phe-Gly-Pro-Cys-Ile-Leu-NH₂
                      |
H-Leu-Leu-Phe-Gly-Pro-Cys-Ile-Leu-NH₂                      (homodimer of SEQ ID NO:24);

H-Leu-Leu-Phe-Gly-Pro-Cys-Ile-Leu-OAllyl
                      |
H-Leu-Leu-Phe-Gly-Pro-Cys-Ile-Leu-OAllyl                   (homodimer of SEQ ID NO:23);

H-Leu-Leu-Phe-Gly-Pro-Cys-Ile-Leu-Asn-NH₂
                      |
H-Leu-Leu-Phe-Gly-Pro-Cys-Ile-Leu-Asn-NH₂                  (homodimer of SEQ ID NO:25);

H-Leu-Leu-Phe-Gly-Pro-Cys-Ile-Leu-Asn-Arg-OH
                      |
H-Leu-Leu-Phe-Gly-Pro-Cys-Ile-Leu-Asn-Arg-OH               (homodimer of SEQ ID NO:26);

H-Phe-Leu-Phe-Gly-Pro-Cys-Ile-Leu-Asn-NH₂
                      |
H-Phe-Leu-Phe-Gly-Pro-Cys-Ile-Leu-Asn-NH₂                  (homodimer of SEQ ID NO:27);

H-Leu-Leu-Phe-Gly-Pro-Cys-Ile-Leu-Asn-Arg-Leu-Met-Glu-NH₂
                      |
H-Leu-Leu-Phe-Gly-Pro-Cys-Ile-Leu-Asn-Arg-Leu-Met-Glu-NH₂  (homodimer of SEQ ID NO:28);

H-Phe-Leu-Phe-Gly-Pro-Cys-Ile-Leu-Asn-Arg-Leu-Met-Glu-NH₂
                      |
H-Phe-Leu-Phe-Gly-Pro-Cys-Ile-Leu-Asn-Arg-Leu-Met-Glu-NH₂  (homodimer of SEQ ID NO:29); and Fmoc-Phe-Leu-Phe-Gly-Pro-Cys-Ile-Leu-Asn-Arg-Leu-Met-Glu-NH₂
                         |
Fmoc-Phe-Leu-Phe-Gly-Pro-Cys-Ile-Leu-Asn-Arg-Leu-Met-Glu-NH₂  (homodimer of SEQ ID NO:29).
```

5. A homodimer selected from the group consisting of:

```
H-Gly-Pro-Cys-Ile-OH
          |
H-Gly-Pro-Cys-Ile-OH                                       (homodimer of SEQ ID NO:1);

H-Leu-Leu-Phe-Gly-Pro-Cys-Ile-OH
                      |
H-Leu-Leu-Phe-Gly-Pro-Cys-Ile-OH                           (homodimer of SEQ ID NO:8);

H-Leu-Leu-Tyr-Ser-Pro-Cys-Phe-OH
                      |
H-Leu-Leu-Tyr-Ser-Pro-Cys-Phe-OH                           (homodimer of SEQ ID NO:18); and H-Leu-Leu-Phe-Gly-Pro-Cys-Ile-Leu-Asn-Arg-Leu-Met-Glu-NH₂
                      |
H-Leu-Leu-Phe-Gly-Pro-Cys-Ile-Leu-Asn-Arg-Leu-Met-Glu-NH₂  (homodimer of SEQ ID NO:28).
```

6. A homodimer selected from the group consisting of:

```
H-Leu-Leu-Phe-Gly-Pro-Cys-Ile-OH
                      |
H-Leu-Leu-Phe-Gly-Pro-Cys-Ile-OH  (homodimer of
                                   SEQ ID NO:8);
                                   and
H-Leu-Leu-Tyr-Ser-Pro-Cys-Phe-OH
                      |
H-Leu-Leu-Tyr-Ser-Pro-Cys-Phe-OH  (homodimer of
                                   SEQ ID NO:18).
```

7. A pharmaceutical composition comprising the homodimer of claim 2 and a pharmaceutically acceptable carrier.

8. A homodimer of claim 3 wherein

X is Gly, Y is Pro and Z is Ile;

X is Ala, Y is Pro and Z is Ile;

X is Arg, Y is Pro and Z is Ile;

X is Asp, Y is Pro and Z is Ile;

X is Trp, Y is Pro and Z is Ile;

X is Ser, Y is Pro and Z is Phe; or

X is Gly, Y is Pro and Z is Pro.

9. A pharmaceutical composition comprising the homodimer of claim 2 and a pharmaceutically acceptable carrier.

10. A pharmaceutical composition comprising the homodimer of claim 3 and a pharmaceutically acceptable carrier.

11. A pharmaceutical composition comprising the homodimer of claim 4 and a pharmaceutically acceptable carrier.

12. A pharmaceutical composition comprising the homodimer of claim 5 and a pharmaceutically acceptable carrier.

13. A pharmaceutical composition comprising the homodimer of claim 6 and a pharmaceutically acceptable carrier.

14. A pharmaceutical composition comprising the homodimer of claim 8 and a pharmaceutically acceptable carrier.

* * * * *